United States Patent
Furman et al.

(10) Patent No.: US 7,804,590 B2
(45) Date of Patent: *Sep. 28, 2010

(54) MULTI MODE INSPECTION METHOD AND APPARATUS

(75) Inventors: Dov Furman, Rehovot (IL); Noam Dotan, Givatayim (IL); Efraim Miklatzky, Jerusalem (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 12/316,302

(22) Filed: Dec. 10, 2008

(65) Prior Publication Data

US 2009/0091749 A1 Apr. 9, 2009

Related U.S. Application Data

(63) Continuation of application No. 11/895,204, filed on Aug. 22, 2007, now Pat. No. 7,480,039, which is a continuation of application No. 11/176,844, filed on Jul. 6, 2005, now Pat. No. 7,274,444.

(60) Provisional application No. 60/587,675, filed on Jul. 12, 2004.

(51) Int. Cl.
*G01N 21/00* (2006.01)
(52) U.S. Cl. ............................ 356/237.1; 356/237.2
(58) Field of Classification Search .... 356/237.1–237.5
See application file for complete search history.

(56) References Cited

U.S. PATENT DOCUMENTS

| 2001/0033386 A1* | 10/2001 | Kranz et al. | 356/601 |
| 2003/0227618 A1* | 12/2003 | Some | 356/237.1 |
| 2004/0032581 A1* | 2/2004 | Nikoonahad et al. | 356/237.2 |
| 2005/0084766 A1* | 4/2005 | Sandstrom | 430/5 |

* cited by examiner

*Primary Examiner*—Michael P Stafira
(74) *Attorney, Agent, or Firm*—Sonnenschein Nath & Rosenthal LLP

(57) ABSTRACT

An inspection system for inspecting an object, the system comprising an illuminator including at least one pulsed light source, a detector assembly, and a relative motion provider operative to provide motion of the object relative to the detector assembly, along an axis of motion, the detector assembly comprising a plurality of 2-dimensional detector units whose active areas are arranged at intervals.

12 Claims, 11 Drawing Sheets

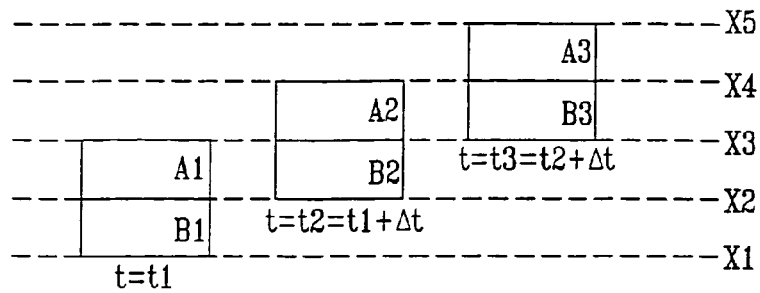
FIG. 1
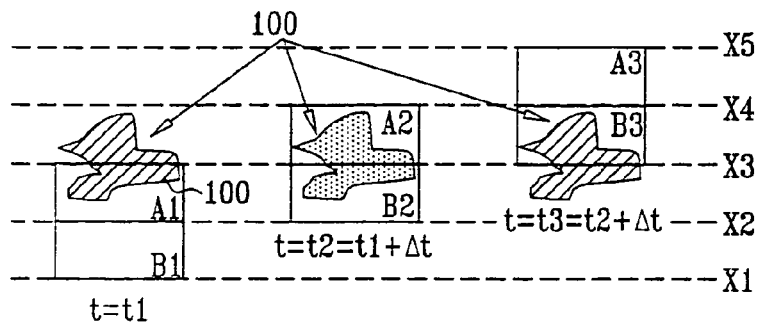
FIG. 2A
FIG. 2B
FIG. 3
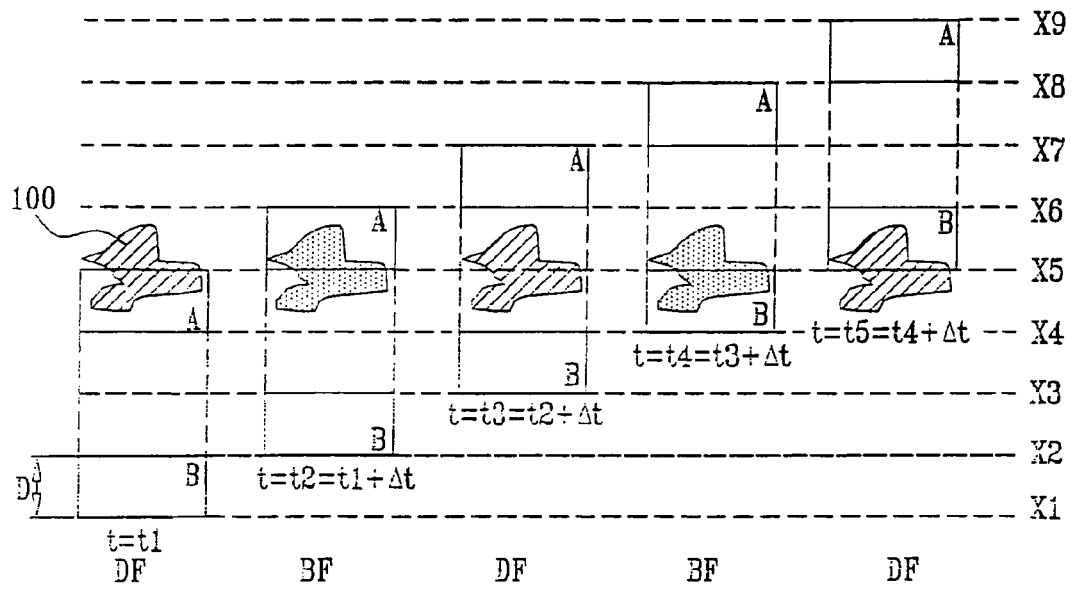

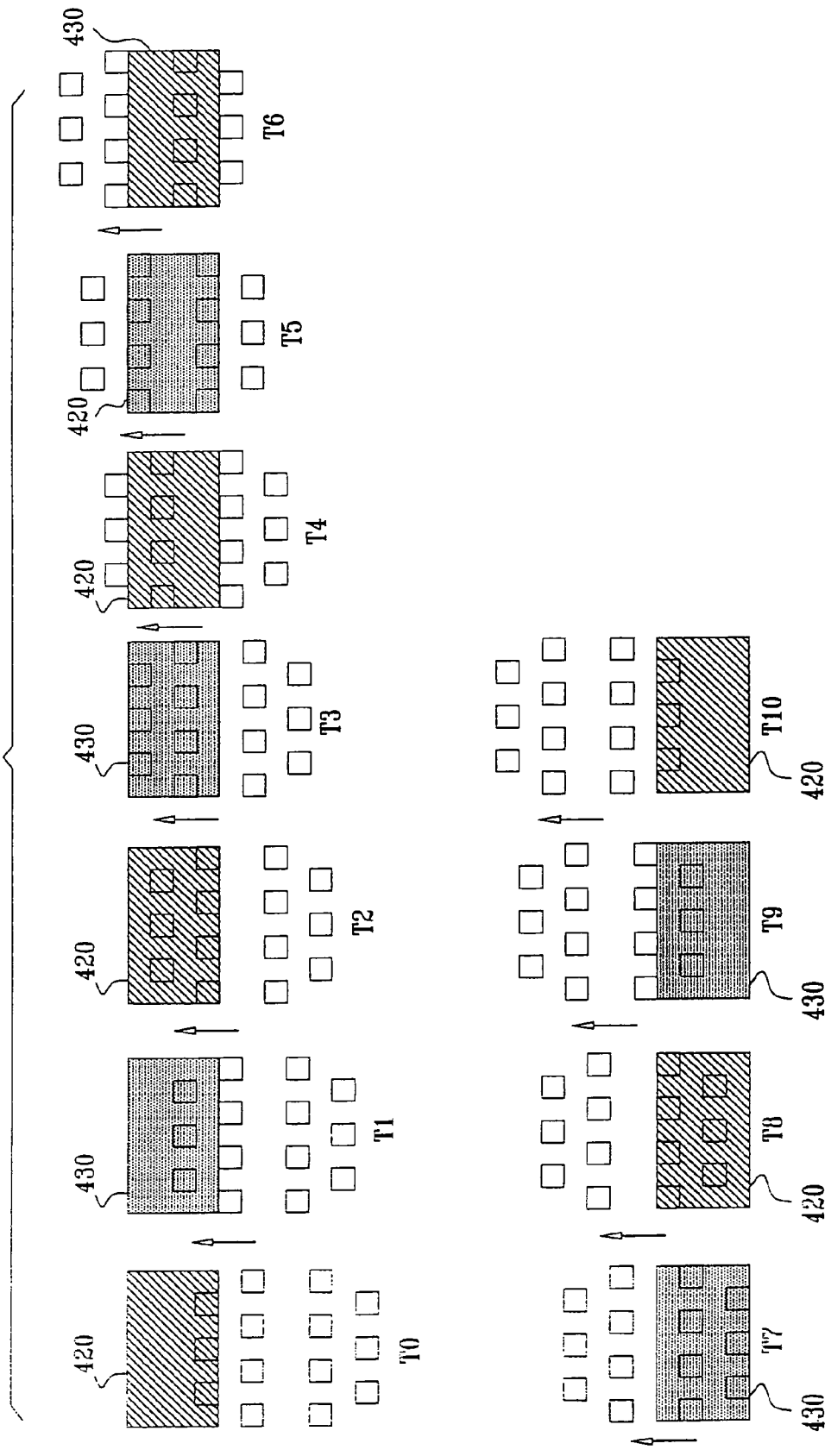

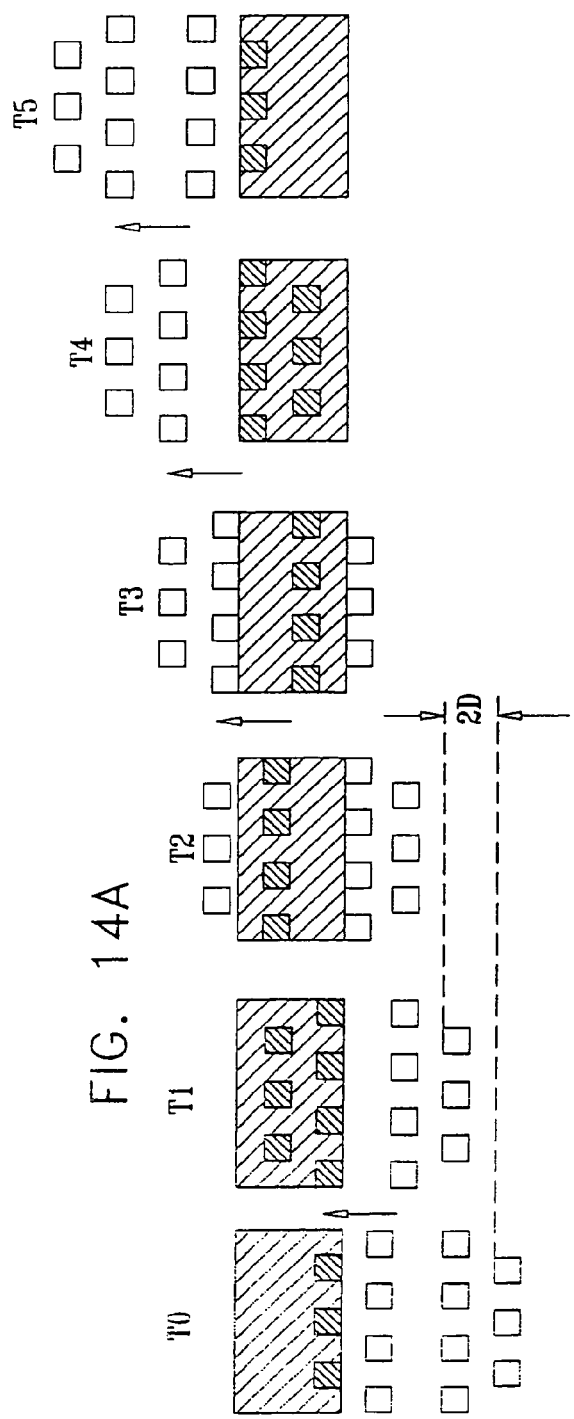
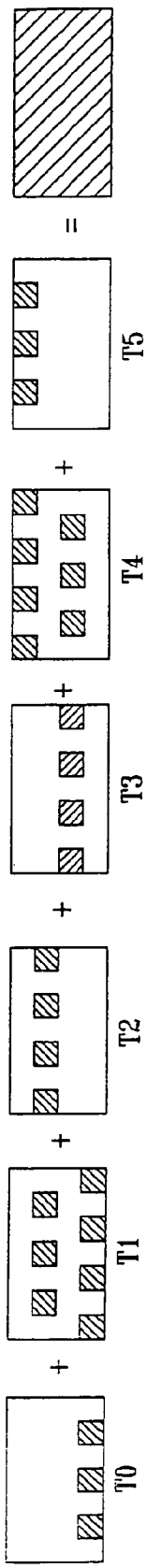
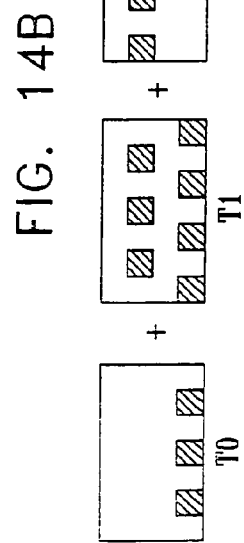
FIG. 14A
FIG. 14B
FIG. 14C

MULTI MODE INSPECTION METHOD AND APPARATUS

CROSS REFERENCE TO RELATED APPLICATIONS

This application is a Continuation Application of U.S. patent application Ser. No. 11/895,204 filed Aug. 22, 2007, now U.S. Pat. No. 7,480,039 which is a continuation of U.S. patent application Ser. No. 11/176,844, filed Jul. 6, 2005, now issued as U.S. Pat. No. 7,274,444.

REFERENCE TO COPENDING APPLICATIONS

This application claims priority of U.S. Ser. No. 60/587,675, filed Jul. 12, 2004.

FIELD OF THE INVENTION

The present invention relates to methods and apparatus for multi mode inspection of an article such as a semiconductor wafer or reticle.

BACKGROUND OF THE INVENTION

State of the art methods and apparatus for inspection of an article such as a semiconductor wafer or reticle or printed circuit board (PCB) are described in the following patent documents: U.S. Pat. Nos. 6,816,249; 6,288,780; 5,116,479; published US Application No. 2004/0027688. The disclosures of all publications mentioned in the specification and of the publications cited therein are hereby incorporated by reference.

SUMMARY OF THE INVENTION

When inspecting semi conductor wafer, reticles, or PCBs, different modes of illumination such as bright field (BF) reflection mode, dark field (DF) reflection mode or bright field and dark field transmissive mode, add more information with which different type of defects can be detected. Many types of defects are seen more clearly in one illumination mode. For example small change in dielectric transparent layer thickness have a large effect on the reflected bright field signal due to thin layer effect, but yield very low dark field scattering signal due to low edge profile.

In other cases certain types of defects are considered to have only nuisance value, since they have no effect on the product function or production yield, while other defects are considered 'killer defects' since they have a large effect on the product function or production yield. Many times these two types of defects yield different signals in different modes of illumination. Therefore by combining the information obtained from various illumination modes, one can filter out nuisance defects from real defects and more generally, differentially weight defects yielded by various different modes of inspection.

It is very useful to analyze all the information from an inspected object together, to yield better detection, rather than to inspect the object first in one mode, detecting all relevant defects and then to inspect in another mode, detecting more defects and then process the information.

One example of the use of the combined information is to filter out metal grains. DF inspection is very sensitive to small particles, but is also sensitive to metal grains on metal surfaces, which usually are considered to have only nuisance value. DF images usually do not provide good segmentation data to differentiate between the different features on the wafer. Therefore, it is very hard to know if a defect lay on top of metal line or on a dielectric surface. The BF image usually enables differentiation between a metal line and dielectric due to the difference in image gray level. Thus the BF image can provide the segmentation data, showing if the defect is located on a metal line or not. If the defect found in DF is located on a metal line it is suspected to be metal grain and may be filtered out of the defect list.

To be able to process all the information together one should either store all the data from one inspection and use it when the next inspection data is available or generate more than one imaging mode data simultaneously. The first option is not realistic due to the very high volume of memory required and the other option complicates the inspection tool, since it involves having at least two parallel imaging devices operating at the same time.

The present invention seeks to provide at least two operationally simple imaging modes.

There is thus provided, in accordance with a preferred embodiment of the present invention, an inspection system for inspecting an object, the system comprising an illuminator including at least one pulsed light source; a detector assembly; and a relative motion provider operative to provide motion of the object relative to the detector assembly, along an axis of motion; the detector assembly comprising a plurality of 2-dimensional detector units whose active areas are arranged at intervals, wherein preferably, each detector has a dimension d along the axis of motion, and the interval between each pair of adjacent detectors is other than overhead an even integer multiple of d. It is appreciated that the detectors may have an interval between them which is somewhat smaller than an even integer multiple of d, in which case a certain amount of overhead or overlap is provided.

Further in accordance with a preferred embodiment of the present invention, the illuminator operates in a dark-field illumination mode.

Still further in accordance with a preferred embodiment of the present invention, the illuminator operates in a bright-field illumination mode.

Further in accordance with a preferred embodiment of the present invention, the illuminator selectively provides at least one mode of illumination according to an illumination schedule and the relative motion provider provides motion of the object relative to the detector assembly according to a motion schedule, and the motion schedule and the illumination schedule are selected to provide images of the entirety of the object, in at least one mode of illumination. Also provided in accordance with another preferred embodiment of the present invention, is an inspection system for inspecting an object, the system comprising an illuminator, including at least one pulsed light source, selectively providing at least one mode, and optionally a plurality of modes, of illumination according to an illumination schedule; a detector assembly; and a relative motion provider operative to provide motion of the object relative to the detector assembly, along an axis of motion, at a velocity v; the detector assembly comprising a plurality (n) of 2-dimensional detector units each having an active area, wherein detector units disposed adjacently along the axis of motion provide a linear sequence of adjoining active detector areas along the axis of motion, and wherein the velocity v and the illumination schedule are selected to provide images of the entirety of the object, in a particular illumination mode or in each the plurality of modes of illumination.

Further in accordance with a preferred embodiment of the present invention, said at least one light source operates in a plurality of modes of illumination.

Still further in accordance with a preferred embodiment of the present invention, the illumination schedule comprises alternation of the plurality of modes of illumination.

Additionally in accordance with a preferred embodiment of the present invention, the illumination schedule comprises a sequence of pulses wherein exactly one of the at least one light sources operates per pulse, in a predetermined order.

Further in accordance with a preferred embodiment of the present invention, the detector assembly comprises a single detector and the plurality of 2-dimensional detector units comprise equal-sized portions of the single detector defined in a linear sequence along the axis of motion.

Still further in accordance with a preferred embodiment of the present invention, each such detector unit comprises a separate detector.

Further in accordance with a preferred embodiment of the present invention, the system comprises electronic memory for storing images of portions of the object detected by the detector assembly; and an image combiner operative to combine a plurality of images generated by the plurality of illumination modes respectively, of a specific portion of the object; wherein the electronic memory is operative to allow images of first object portions to override images of second object portions which have already been processed by the image combiner.

Additionally in accordance with a preferred embodiment of the present invention, the illuminator comprises a single light source directed, according to the illumination schedule, toward a plurality of illumination optics corresponding to the plurality of illumination modes respectively.

Further in accordance with a preferred embodiment of the present invention, the at least one light source comprises a plurality of light sources.

Further in accordance with a preferred embodiment of the present invention, the plurality of modes of illumination include at least one dark mode.

Still further in accordance with a preferred embodiment of the present invention, the plurality of modes of illumination include at least one bright mode.

Additionally in accordance with a preferred embodiment of the present invention, the plurality of modes of illumination include a plurality of dark modes differing in their polarizations.

Still further in accordance with a preferred embodiment of the present invention, the plurality of modes of illumination include at least one transmissive illumination mode.

Additionally in accordance with a preferred embodiment of the present invention, the plurality of modes of illumination include at least one reflective mode.

Also provided, in accordance with another preferred embodiment of the present invention, is a method for inspecting a microscopic object, the method comprising: providing a first plurality of 2-dimensional detector units which define a corresponding first plurality of fields of view; providing motion of the object relative to the first plurality of detector units in accordance with a motion schedule and in a selected motion pattern; providing at least one pulsed illumination mode; and selecting a pulsed illumination schedule according to which the first plurality of fields of view are illuminated in at least one illumination mode and arranging the first plurality of detector units, so as to provide complete coverage of the object as illuminated in the at least one illumination mode.

Further in accordance with a preferred embodiment of the present invention, a second plurality of illumination modes is provided and the illumination schedule is selected such that the first plurality of fields of view is illuminated in individual ones of the second plurality of illumination modes at various times within the course of a single pass over the object, and wherein the first plurality of detector units is arranged and the illumination schedule selected, so as to provide complete coverage of the object as illuminated in each of the second plurality of illumination modes, in the course of the single pass over the object.

Still further in accordance with a preferred embodiment of the present invention, the selected motion pattern typically comprises a snake path up and down imaginary slices defined along the object.

Further in accordance with a preferred embodiment of the present invention, the complete coverage of the object comprises information yielded by each of the second plurality of illumination modes and wherein the method also comprises combining local information yielded by at least two of the second plurality of illumination modes, thereby to generate combined information regarding individual object locations.

Still further in accordance with a preferred embodiment of the present invention, the method also comprises using the combined information to filter out nuisance defects and retain real defects.

Further in accordance with a preferred embodiment of the present invention, the method also comprises using the combined information to filter out metal grains.

Still further in accordance with a preferred embodiment of the present invention, the plurality of 2-dimensional detector units is arranged in at least one column disposed along the axis of motion.

Further in accordance with a preferred embodiment of the present invention, the at least one column comprises a single column or alternatively a plurality of columns.

Further in accordance with a preferred embodiment of the present invention, the at least one illumination mode comprises a single pulsed illumination mode or a plurality of illumination modes.

Still further in accordance with a preferred embodiment of the present invention, the plurality of illumination modes includes first and second illumination modes and at least one first threshold value is used to filter candidate defects thereby to generate a first defect list from images generated in the first illumination mode and at least one second threshold value is used to filter candidates defects thereby to generate a second defect list from images generated in the second illumination mode and wherein at least one first threshold value used in at least a first image portion is determined at least partly by information characterizing the at least one first image portion as illuminated in the second illumination mode, and wherein at least one second threshold value used in at least a second image portion is determined at least partly by information characterizing, the at least one second image portion as illuminated in the first illumination mode.

Further in accordance with a preferred embodiment of the present invention, the detector assembly generates an output representing the object, and the system also comprises a first inspection channel using a first illumination mode and identifying defects in the output of the detector assembly using a first, location dependent, detection sensitivity function and a second inspection channel using a second illumination mode and identifying defects in the output of the detector assembly using a second, location dependent, detection sensitivity function, wherein the first function is at least partly determined by the second channel and wherein the second function is at least partly determined by the first channel.

Also provided, in accordance with another preferred embodiment of the present invention, is a multi-mode inspection system comprising: a first inspection channel using a first illumination mode and identifying defects using a first, location dependent, detection sensitivity function; and a second inspection channel using a second illumination mode and identifying defects using a second, location dependent, detection sensitivity function; wherein the first function is at least partly determined by the second channel and wherein the second function is at least partly determined by the first channel.

According to a preferred embodiment of the present invention, at least one of the first and second functions comprises a die-to-die comparison based function.

According to a preferred embodiment of the present invention, at least one of the first and second functions comprises a cell-to-cell comparison based function.

According to a preferred embodiment of the present invention, at least one of the first and second functions comprises a die-to-multidie comparison based function.

According to a preferred embodiment of the present invention, the detector assembly generates an output representing the object, the system also comprising, a defect detector operative to detect defects in the output of the detector assembly. The defect detector may be based on a die to die comparison process and/or a cell to cell comparison process and/or a die to multi-die comparison process.

Further in accordance with a preferred embodiment of the present invention, the even integer multiple of d is 2Md and wherein the pulsed light source is triggered to provide a pulse each time the object travels, relative to the detector assembly, a distance of 2M times the field of view extended by each of the plurality of 2-dimensional detector units.

Also provided, in accordance with another preferred embodiment of the present invention, is an inspection method for inspecting an object, the method comprising providing an illuminator including at least one pulsed light source and a detector assembly comprising a plurality of 2-dimensional detector units whose active areas are arranged at intervals and providing motion of the object relative to the detector assembly, along an axis of motion.

Further in accordance with a preferred embodiment of the present invention, the method comprises employing the illuminator to provide at least one mode of illumination according to an illumination schedule, wherein motion of the object relative to the detector assembly is provided according to a motion schedule and the method also comprises selecting the motion schedule and the illumination schedule to provide images of the entirety of the object in at least one mode of illumination.

Further in accordance with a preferred embodiment of the present invention, at least one mode of illumination comprises a plurality of modes of illumination and the motion schedule and the illumination schedule are selected to provide images of the entirety of the object, in each of the plurality of modes of illumination.

The term "FOV" (field of view) is used herein to mean a portion of an inspected object which is visible to a detector.

It is appreciated that the present invention is applicable to substantially any type of two-dimensional detector array including but not limited to CCDs and CMOSs and specific references to CCDs are generally understood to be merely by way of example.

BRIEF DESCRIPTION OF THE DRAWINGS

The present invention will be understood and appreciated from the following detailed description, taken in conjunction with the drawings in which:

FIG. 1 is a diagram of a flow of inspection provided in accordance with a preferred embodiment of the present invention;

FIG. 2A is an inspection flow diagram illustrating a feature as viewed by different detectors constructed and operative in accordance with a preferred embodiment of the present invention, at different times;

FIG. 2B is a pictorial illustration of the feature viewed by the detectors in FIG. 2A;

FIG. 3 is an inspection flow diagram illustrating an alternative embodiment of the present invention having two illumination modes, in which two detectors are separated by a distance which is an even multiple of the dimension of the CCD or other detector in the direction of motion;

FIG. 11 is a pictorial illustration of a scanning sequence employing two modes of illumination and the two-dimensional detector array which entirely covers the inspected feature in the field of view of FIG. 10A;

FIG. 14A is a pictorial illustration of a scanning sequence employing only one mode of illumination and the two-dimensional detector array which entirely covers the inspected feature of view of FIG. 10A;

FIG. 14B is a pictorial illustration showing the full coverage provided by the scanning sequence of FIG. 11; and FIG. 14C is a diagram showing the pulse times at which each location within an object portion is covered by the single illumination mode, from among the following pulse times: t0, t1, t2, t3, t4 and t5.

DETAILED DESCRIPTION OF A PREFERRED EMBODIMENT

One preferred embodiment of the present invention typically employs a short pulsed illumination system such as that described in U.S. Pat. No. 6,693,664 to Neumann, assigned to Negevtech, Rehovot, Israel. The short pulse illuminating system typically illuminates the object with repetitive light pulses, while the inspected objects travels at a continuous velocity. The pulsed light source is synchronized with the object moving mechanism in such a way that each time the object travels a distance that is approximately equal to the imaging field of view size, a pulse of light is triggered and an image is acquired.

A detection field of view may be split into two parts in such a way that when properly synchronized with the object motion speed and the pulse of the light source, a feature on the object is imaged first on the first portion of the detector and in a successive pulse is imaged on the second portion of the detector. Thus each feature on the inspected wafer or reticle is imaged twice.

The modes of illumination are now chosen in such a way that the first pulse will be in one mode (for instance BF) and that the second pulse will be in a second mode (for instance DF). In this way each feature is scanned in both modes of illumination. One can extend this to more than two illumination modes. FIG. 1 shows the flows of inspection. A, B denotes the two parts of the detector and the numbers 1, 2, 3 denotes the successive pulse and image numbers. The horizontal direction corresponds to the flow of time or pulses. The vertical direction corresponds to relative motion of the detector and the object.

FIG. 2A shows how the different detectors in the field of view image a specific feature. As can be seen in FIG. 2A each part of the feature is imaged in the two modes of illumination.

The object motion is relative to the imaging device and can be accomplished either with the motion of the object or of the imaging, device. Detector A and B may be two parts of the same 2 dimensional detector.

In the above description the active areas of the detectors covering the FOV (field of view) are adjacent to each other as described in U.S. Pat. No. 6,693,664, but alternatively, the two detectors can be separated by a distance equal to twice the dimension of the CCD in the direction of the motion as seen in FIG. 3.

Figure 4:
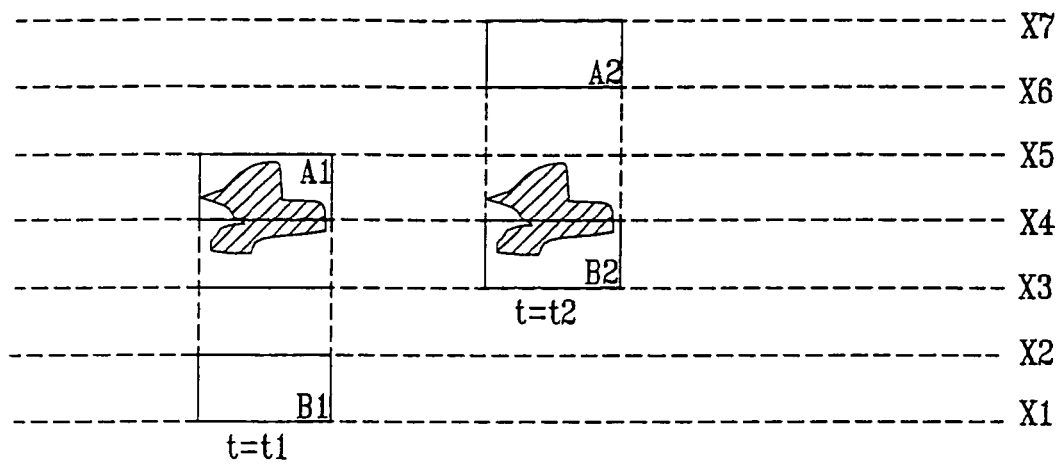
FIG. 4 is an alternative inspection flow diagram in which two detectors, separated by a distance which is an even multiple of the dimension of the CCD or other detector in the direction of motion are used with a different synchronization scheme to provide double speed inspection based on a single illumination mode.

The sequence of the illumination pulses is such that the two types of illuminations alternate from pulse to pulse. In this way a feature that is being imaged by the first pulse by the first illumination mode (t1) is imaged by the fourth pulse by the second illumination mode (t4). When the two detectors are separated by a certain gap one can synchronize the object motion speed and the pulse timing so that a full inspection area without any gaps will take place. For instance if one uses two 2 dimensional detectors positioned in the image plane so that the distance between them in the axis of the object motion is twice the size of the detector in this dimension as shown in FIG. 4 and the illumination pulses are triggered every time the object travels a distance equal to twice the FOV extended by each detector, then the entire inspected area will be covered by the detectors.

Another possible embodiment for two illumination modes in one scan is to illuminate part of the field of view with one mode of illumination and the other part of the field of view with another mode of illumination per each pulse of light.

Figure 5:
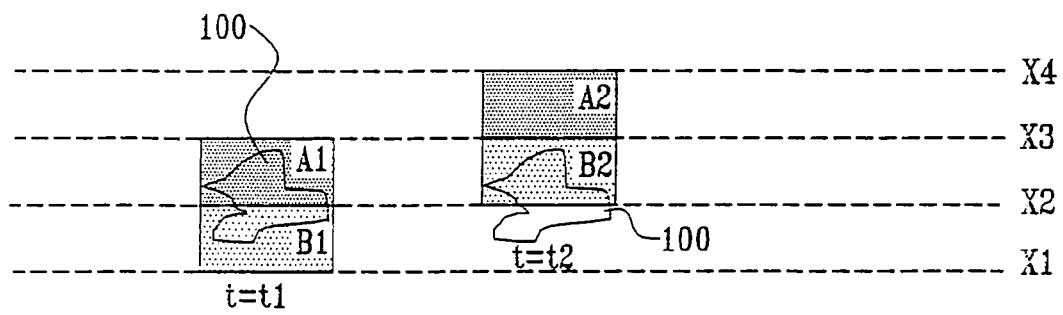
FIG. 5 is an inspection flow diagram illustrating a preferred embodiment of the present invention wherein two illumination modes operate simultaneously, illuminating respective portions of the same field of view.

Typically, detector A in FIG. 5 always images the part of the field of view that is illuminated by the first illumination mode. Detector B always images the part of the field of view that is illuminated by the second illumination mode. By moving the object half the field of view between successive illumination pulses, each feature is imaged twice, once in the first illumination mode and than in the second illumination mode. A combination of field of view illumination and distance between the detectors is possible.

The illumination system can be based on two pulsed light sources such as two ND YAG Q switched lasers, one generating light for the first illumination mode and the second generating light for the second illumination mode. Both lasers are synchronized to trigger a laser pulse one after the other, operatively timed with respect to the object motions. Alternatively, the illumination system may be based on one light source such as an ND YAG Q-switched laser and a beam splitter that divide the light between the first and second illumination modes.

The illumination system can be based on one light source such as an ND YAG Q switched laser and an optical switch delivering the beam first to the first illumination system and subsequently to the second illumination mirror and so forth. This switch may comprise a mirror directing the beam of light each time to the appropriate illumination system. Alternatively, the switch may comprise an acousto-optic deflector.

The example embodiments shown and described herein are now summarized and preferred embodiments are described:

Each light source may comprise an ND YAG Q-switched laser using $2^{nd}$ or $3^{rd}$ or $4^{th}$ harmonics generation, emitting light in the visible or UV and DUV spectral range. Yet another possible light source is an Excimer laser emitting light in 351 nm or 248 nm or 193 nm.

FIG. 2A shows an example feature or object portion 100, shown in isolation in FIG. 2B, and superimposed thereupon the fields of view A1 and B1 of two two-dimensional detectors A and B respectively. It is appreciated that the active areas hence fields of view, of each detector may, for example, be either square or rectangular. FIG. 2A illustrates the example feature imaged on the two 2-dimensional detectors A and B at different times, as relative motion between the detectors and the object takes place. At a time t1, at which a first illumination pulse is provided by an illumination source, the fields of view of the two detectors are A1 and B1, shown superimposed on a feature 100 appearing on the object to be inspected. FIG. 2A also shows the fields of view A2 and B2 of the same two detectors at a time t2, superimposed on the same feature 100. FIG. 2A also shows the fields of view A3 and B3 of the same two detectors at a time t3, superimposed on the same feature 100. It is appreciated that objects typically include a large number of different features and feature 100 is used exclusively throughout the figures of the present specification merely to simplify description of the invention. X1, X2, X3, ... denote locations along the axis of relative motion between the object to be inspected and the detectors. The relative motion typically follows a "snake path" up and down imaginary slices defined along the object, generally at a uniform velocity v.

Second and third illumination pulses are provided by an illumination source at times t2 and t3 respectively. The three illumination pulses may or may not be provided by a single illumination source. The first and third illumination pulses provide a first mode of illumination as indicated by hatching. The second illumination pulse provide a second mode of illumination as indicated by dotting. More generally, the first and second modes of illumination may alternate, e.g. odd pulses may be provided in the first illumination mode and even pulses may be provided in the second illumination mode.

Due to appropriate selection of the velocity of relative object-detector motion, t2 is the time at which detector B sees what detector A saw at time t1, t3 is the time at which detector B sees what detector A saw at time t2. It is appreciated that A and B may be two separate detectors whose active areas are adjacent. e.g. as described in coassigned U.S. Pat. No. 6,6936,64, or A and B may be two adjacent portions of the same detector. It is appreciated that different illumination modes may be employed at different times. In the illustrated example, a first illumination mode, such as a bright field illumination mode, may alternate with a second illumination mode, such as a dark field illumination mode. As shown, at times t1 and t3, a bright field illumination pulse is employed whereas at time t2 a dark field illumination pulse is employed. If this pattern continues. i.e. a bright field illumination pulse for all odd-numbered pulses and a dark field illumination pulse at all even-numbered pulse, the result will be that individual object portions are illuminated first in bright field and then in dark field, and object portions adjoining these are illuminated first in dark field and then in bright field. Thus, a single pulse of dark field illumination may serve as the second pulse to illuminate one object portion and the first pulse to illuminate a neighboring object portion.

In the inspection scheme of FIG. 5, two illumination modes are utilized simultaneously to create a field of view including two portions A and B, wherein the first portion is illuminated using the first illumination mode and the second portion is simultaneously illuminated using the second illumination mode. The two portions may or may not be adjacent, where non-adjacency is advantageous in preventing "cross talk" between the two illumination modes. The inspection scheme of FIG. 5 may be implemented by suitable programming of the illumination sequence controller 115 of FIG. 6, such that the bright field illumination apparatus associated with laser 110 operates on half of the FOV extended by the detector assembly 105 and the dark field illumination apparatus associated with laser 120 operates simultaneously on the other half of the FOV extended by the detector assembly 105. The speed of relative motion between the object and the inspection device is half the speed used when single mode inspection is performed.

A particular advantage of the above-described preferred embodiment of the present invention is that each object portion is imaged twice, first in a first illumination mode and subsequently, almost immediately, in a second illumination mode. This allows information regarding each object portion yielded by all of the two or more illumination modes to be combined almost immediately. Therefore, at any given time, very little information needs to be stored since information regarding each individual object portion can be discarded as soon as the information combining process has been completed for that object portion. i.e. almost immediately. For example, if the inspection rate is 30 frames per second, the above information can be discarded after some tens of milliseconds.

Figure 6:
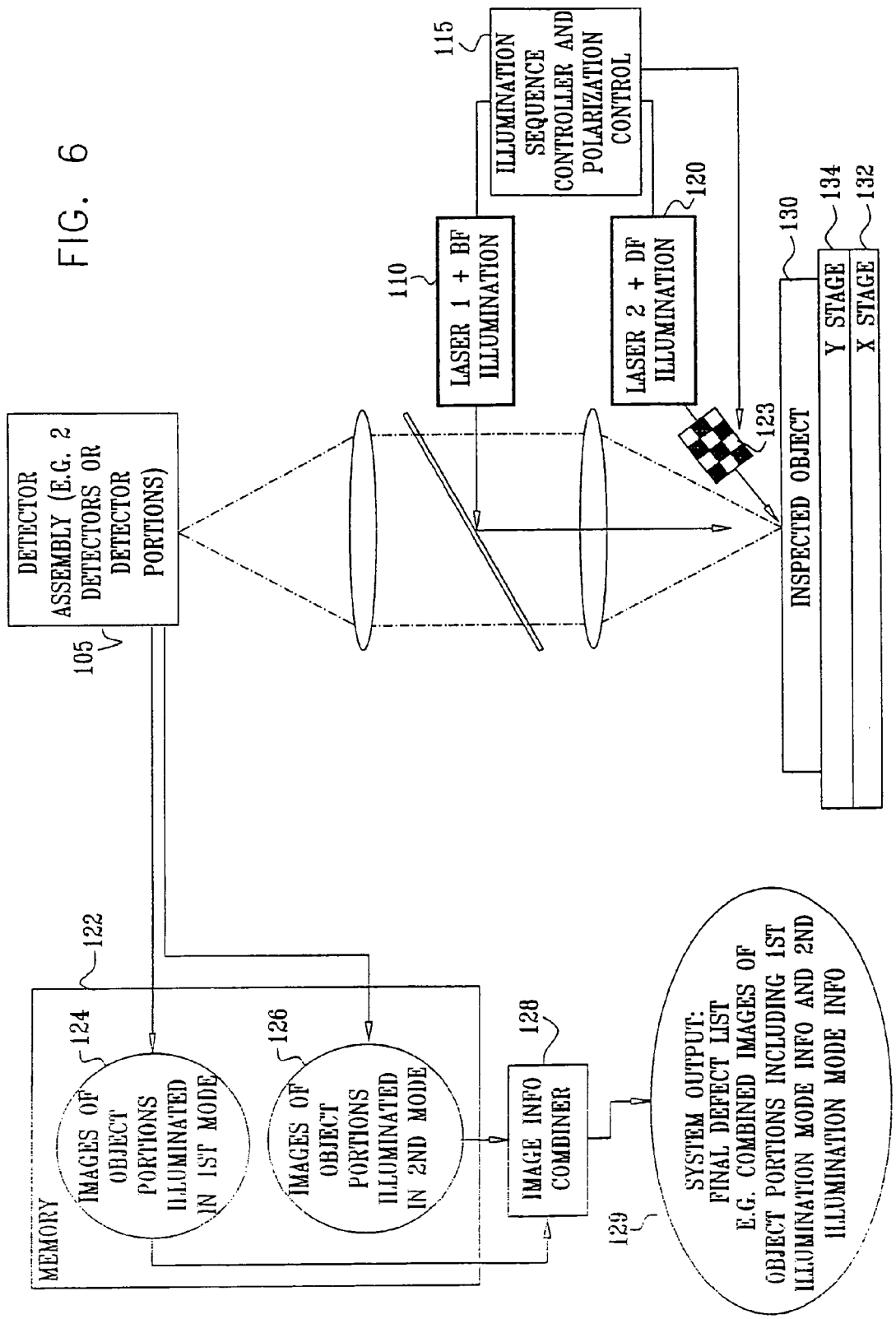
FIG. 6 is a simplified diagram of an illumination system for implementing any of the variations of FIGS. 1-5, constructed and operative in accordance with a first alternative embodiment of the present invention.
Figure 7:
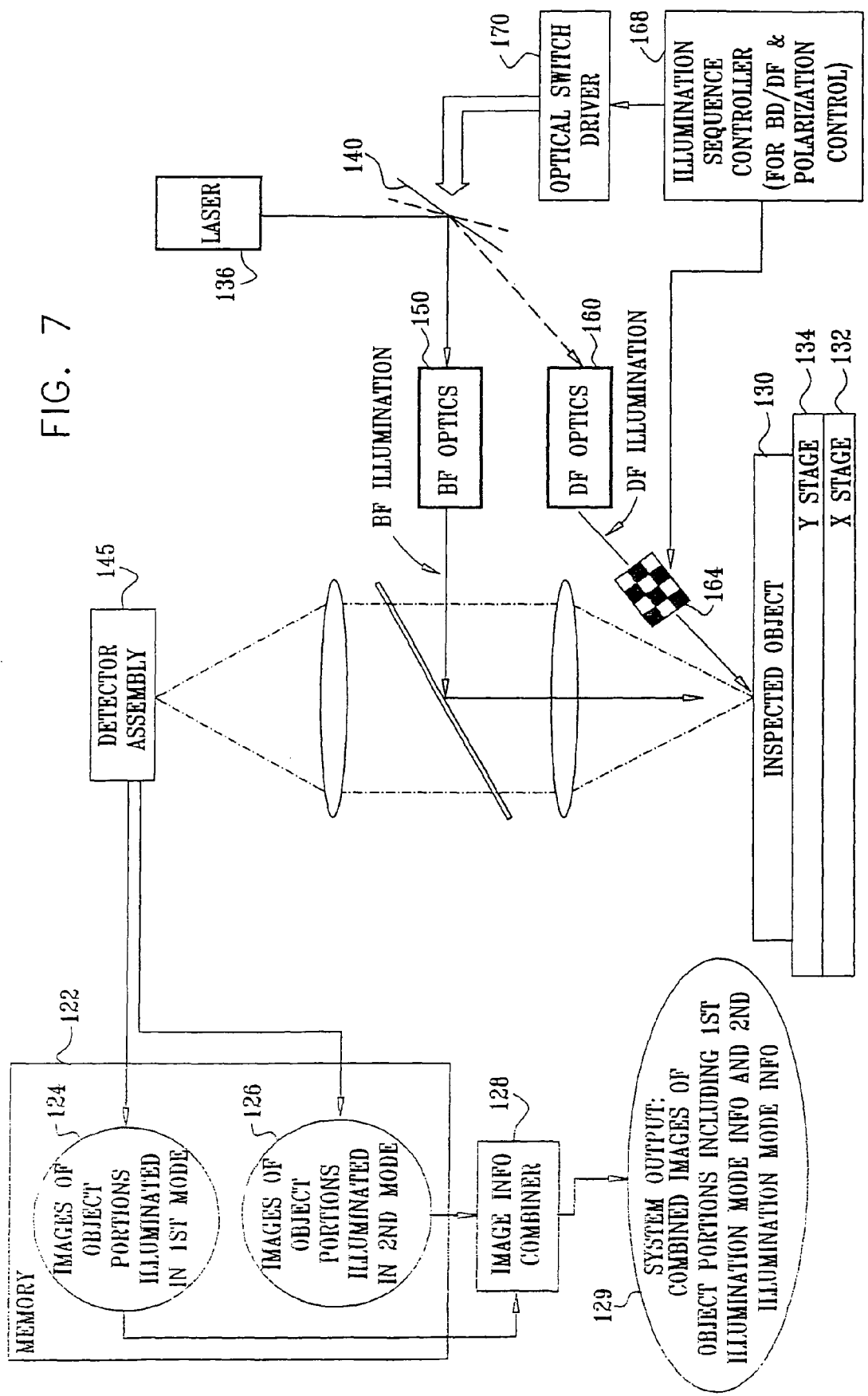
FIG. 7 is a simplified diagram of an illumination system for implementing any of the variations of FIGS. 1-5, constructed and operative in accordance with a second alternative embodiment of the present invention.

The two respective illumination modes can be provided by two separate illumination systems 110 and 120 as shown in FIG. 6, or, as shown in FIG. 7, by a single illumination source 136 which is directed alternatively, e.g. by a rotating mirror 140, to first illumination optics 150 providing the first mode of illumination or to second illumination optics 160 providing the second mode of illumination. According to the embodiment of FIG. 6, two lasers may be operated on alternating pulses, the first laser operating in bright field mode. e.g. at each odd-numbered pulse, and the second in dark field mode, e.g. at each even-numbered pulse. According to the embodiment of FIG. 7, the single laser is operative at all pulses, and its illumination is routed, at alternative pulses, through the first and second illumination optics 150 and 160 respectively.

The velocity of the object-detector relative motion is typically selected to provide a between-pulse distance which is half of the length, along the axis of motion, of the object portion imaged by the detector.

A "slice" is defined as the portion of an object that is imaged in the course of a full length sweep of motion of the object relative to the detector. The length of each slice is typically the length of the sweep of motion of the object relative to the detector and the width of each slice is typically the width of the field of view of the detector. The image of an object may comprise the concatenation of the images of a plurality of slices which cover or partition the object.

When using the above example imaging process, there is defined, in each slice, a sequence of FOV-sized object portions along the axis of motion of the object vs. the detectors ({p1, p2, p3, . . . }, e.g. as shown in FIG. 2B) in which odd-numbered object portions are imaged first in the first illumination mode and substantially immediately afterward in the second illumination mode, whereas even-numbered object portions are imaged first in the second illumination mode and substantially immediately afterward in the first illumination mode.

It is appreciated that similarly, an imaging process may be employed in which three or more generally n illumination modes may be employed. In this case, the detector subsystem comprises a linear sequence, arranged along the axis of object-detector relative motion, of n adjacent detectors or detector portions. If n=3 then once again there is defined, in each slice, a sequence of FOV-sized object portions along the axis of motion of the object vs. the detectors {p1, p2, p3, . . . }.

Object portions in the subsequence {p1, p4, p7, . . . } are imaged first in the first illumination mode and substantially immediately afterward in the second and then third illumination modes. Object portions in the subsequence {p2, p5, p8, . . . } are imaged first in the second illumination mode, then in the third illumination mode and finally in the first illumination mode. Object portions in the subsequent {p3, p6, p9, . . . } are imaged first in the third illumination mode, then in the first illumination mode and finally in the second illumination mode. n similar subsequences may be defined for the more (general case n. The velocity of the object-detector relative motion is selected to provide a between-pulse distance which is 1/n of the length, along the axis of motion, of the object portion imaged by the detector. The distance between slices is the dimensions along an axis perpendicular to the axis of motion, of the object portion imaged by the detector, irrespective of the number of illumination modes employed.

The present invention is suitable for implementing pulsed, 2D-detector inspection processes using any suitable number and type of illumination modes. For example, illumination modes may include a plurality of dark field illumination modes having different respective polarizations. Also, reflective (bright field or dark field) illumination modes may be employed, as well as a transmissive illumination mode.

As described above, to implement n inspection modes, n detectors with adjoining active areas may be employed, arranged in a linear sequence along the axis of relative object-detector motion. Alternatively, as shown in FIG. 3, n detectors or detector portions may be used. These may comprise n adjacent portions of the detector's active area, the portions being arranged in a linear sequence along the axis of relative motion. According to another preferred embodiment of the present invention, however, n detectors may be used whose active areas are not adjoining. Instead, the distance between active areas may be an even integer multiple, such as 2 as shown in FIG. 3, of the dimension, along the direction of motion, of the object portion imaged by the detector.

In the example illustrated in FIG. 3, the distance between active areas of the detector is twice the dimension d, along the direction of motion, of the object portion imaged by the detector. The example shows a feature having two portions p1 and p2 (FIG. 2B), as it is viewed by two detectors A and B whose active areas are separated by a distance 2d. FIG. 3 shows the views at times t1 to t5 respectively, which are the times of occurrence of pulses 1 to 5 respectively. Odd-numbered pulses are in a first illumination mode such as DF, whereas even-numbered pulses are in a second illumination mode such as BF. As shown, at time t1, detector A sees a DF-illuminated p1. At time t2, detector A sees BF-illuminated p2. At time t3, detector A sees neither P1 nor P2, and nor does detector B. At time t4, B sees a BF-illuminated p1. At time t5, B sees a DF-illuminated pa. In summary, p1 is shown DF-illuminated at t1 and BF-illuminated at t4, whereas p2 is shown BF-illuminated at t2 and DF-illuminated at t5. In summary, each object portion is imaged by both of the two illumination modes.

The embodiment of FIG. 3, which may be implemented by the apparatus of FIG. 7 or FIG. 8, inter alia, may be employed to implement object inspection using only a single illumination mode, as shown in FIG. 4. Preferably, the velocity of object-detector relative motion is selected so as to prevent "gaps" (non-imaged object portions). Specifically, if the distance between detectors is m times the length of the detector in the direction of motion, an illumination pulse is triggered each time the object travels a distance of 2m times the FOV extended by each detector. So, for example, if m=1, then a sequence of FOV-length object portions a, b, c, d, ... arranged in the direction of motion will be imaged at the following pulse times respectively: t1, (not imaged), t2, t1, t3, t2, t4, t3, t5, t4, t6, t5, t7, t6, ... tk, t(k−1), t(k+1), tk, ... where tk is the time of occurrence of the k'th pulse. It is appreciated that substantially full coverage of the object is achieved in that gaps may occur only very adjacent to the edge, e.g. only object portion b is a gap in the above example.

In the embodiment of FIG. 5, two illumination modes are operative simultaneously. At each pulse, the first illumination mode illuminates the FOV or FOV portion seen by detector 1/detector portion 1, and simultaneously, the second illumination mode illuminates the FOV or FOV portion seen by detector 2/detector portion 2. A suitable inspection system for implementing the embodiment of FIG. 5 is described below with reference to FIG. 7.

Reference is now made to FIG. 6 which is a simplified block/optical diagram of a defect detection system constructed in accordance with a preferred embodiment of the present invention and operative to implement the embodiments of FIGS. 1-5. The system of FIG. 6 includes a detector assembly 105 which includes an array of detectors constructed and operative as described above with reference to any of the embodiments of FIGS. 1-5, e.g. two or more detectors or detector portions which may or may not have adjacent active areas. Illumination systems 110 and 120 are operatively associated with an illumination sequence controller 115 constructed and operative as described above with reference to any of the embodiments of FIGS. 1-5. Illumination system 110 preferably comprises a first laser and associated bright field illumination and illumination system 120 preferably comprises a second laser and associated dark field illumination. An inspected object 130 is preferably mounted on an X-stage 132 and a Y-stage 134 to provide relative motion, typically in a snake path, of the object 130 relative to the optical components of the system (105, 110, 120).

Optionally, the apparatus of FIG. 6 includes a variable polarizer 123 such as a Pockel magneto-optical device disposed along the optical path of the dark field illumination apparatus 120 which is operative to selectably change the polarization direction of the dark-field light incident upon the object to be inspected. The illumination sequence controller 115, which is typically operative to control the sequence of illumination modes provided by selectively changing the mode of illumination from BF to DF and back, can alternatively or additionally selectively chance the polarization of the DF illumination. The controller 115 is typically programmed in accordance with internal parameters characterizing each inspection session.

Images generated by the detector assembly 105 are typically stored in memory, including images 124 illuminated in the first mode of illumination and images 126 illuminated in the second mode of illumination. The information from the various modes or inspection is combined by an image information combiner 128 and the system's output comprises images of each portion of the object to be inspected, including both first illumination mode information and second illumination mode information. Typically, as described in detail below, combination of image information comprises defect detection sensitivity computation, computed for each illumination mode separately, based on information arriving from the other illumination mode/s.

FIG. 7 is a block/optical diagram of a variation on the system of FIG. 6 in which only a single laser 136 is provided. Optionally the apparatus of FIG. 7 includes a variable polarizer 164 such as a Pockel magneto-optical device disposed along the optical path of the dark field illumination apparatus which is operative to selectably change the polarization direction of the dark-field light incident upon the object to be inspected. An illumination sequence controller 168 is typically operative to control the sequence of illumination modes provided by selectively changing the mode of illumination from BF to DF and back (via optical switch driver 170), and/or by selectively changing, the polarization of the DF illumination. The controller 168 is typically programmed in accordance with internal parameters characterizing each inspection session.

The single illumination source 136 is directed alternatively, e.g. by a rotating mirror 140 actuated by optical switch driver 170, to first illumination optics 150 providing, the first mode of illumination or to second illumination optics 160 providing the second mode of illumination. The illumination generated is thereby routed, at alternative pulses, through the first and second illumination optics 150 and 160 respectively.

Figures 8A, 8B, 8C:
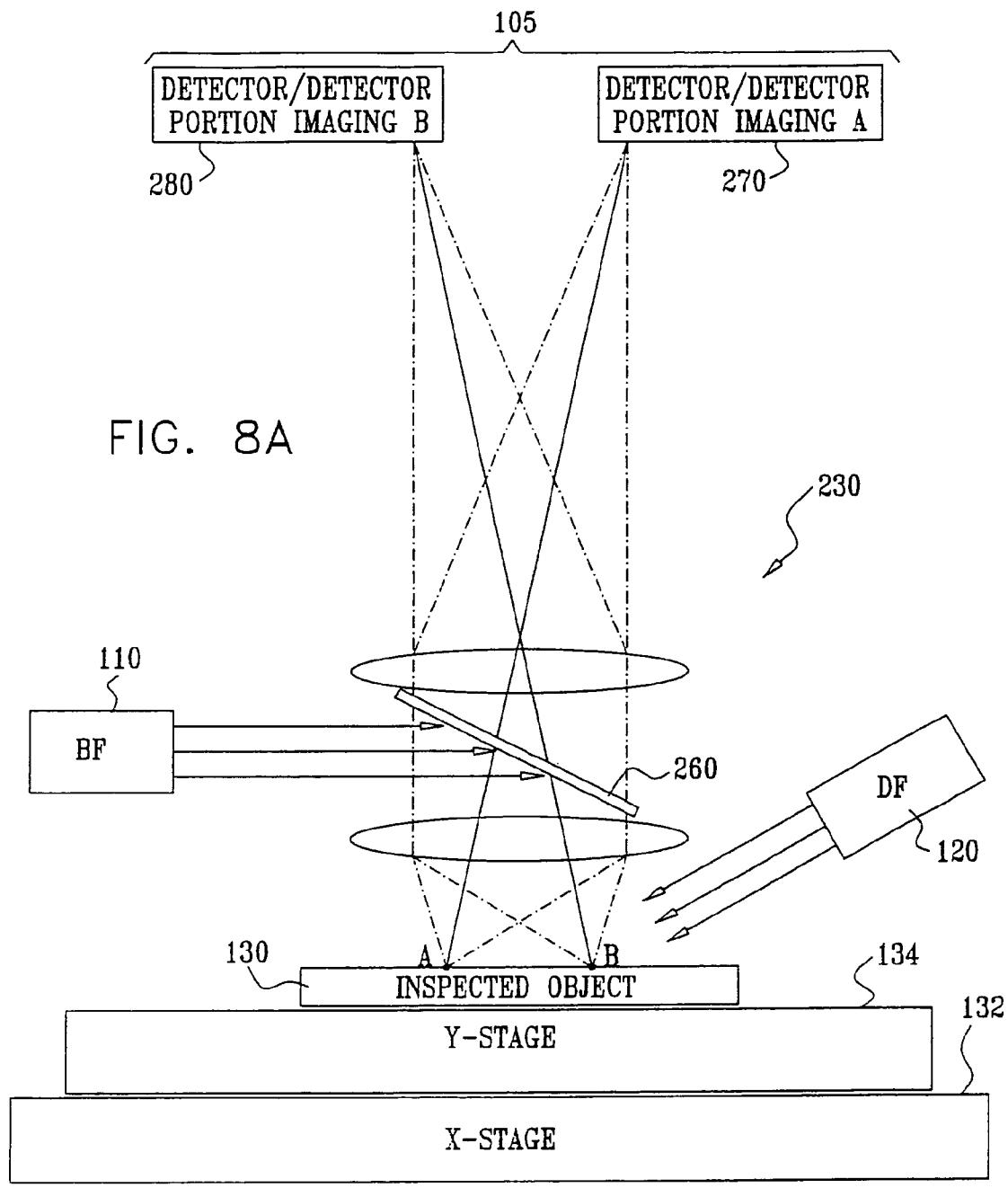
FIG. 8A is a simplified optical diagram illustrating a preferred mode of operation of the illumination system of FIG. 6.
FIGS. 8B and 8C are pictorial illustrations of alternative one-dimensional field of view arrays generated by the detector arrays of FIG. 6 or 7 in accordance with a preferred embodiment of the present invention.

Reference is now made to FIGS. 8A-8C which illustrate preferred modes of operation of the apparatus of FIG. 6. FIG. 8A is an optical diagram of the apparatus of FIG. 6, showing the detector assembly 105 which, according to a preferred embodiment of the present invention, includes two detectors or detector portions 270 and 280. In the illustrated embodiment, dark field illumination is directed toward the inspected object at an oblique angle whereas bright field illumination is directed toward the inspected object via a beam splitter 260. Detector/detector portion 270 images a 2D location A on the inspected object while detector/detector portion 280 simultaneously images a 2D location B, typically of equal dimensions, on the inspected object.

According to a first embodiment of the present invention, described above with reference to FIGS. 1-2A, locations A and B adjoin as shown in FIG. 8B. According to a second embodiment of the present invention, described above with reference to FIG. 3, locations A and B are separated e.g. by a gap whose length is twice the length of A or of B. It is appreciated that the apparatus of FIGS. 8A and 8C is also suitable for implementing FIG. 4 except that in the embodiment of FIG. 4, the two illumination modules are identical rather than operating in different illumination modes as in FIG. 8A.

It is appreciated that the fields of view illustrated in FIGS. 8B and 8C may also be implemented using detector assembly 145 of FIG. 7.

Figure 9:
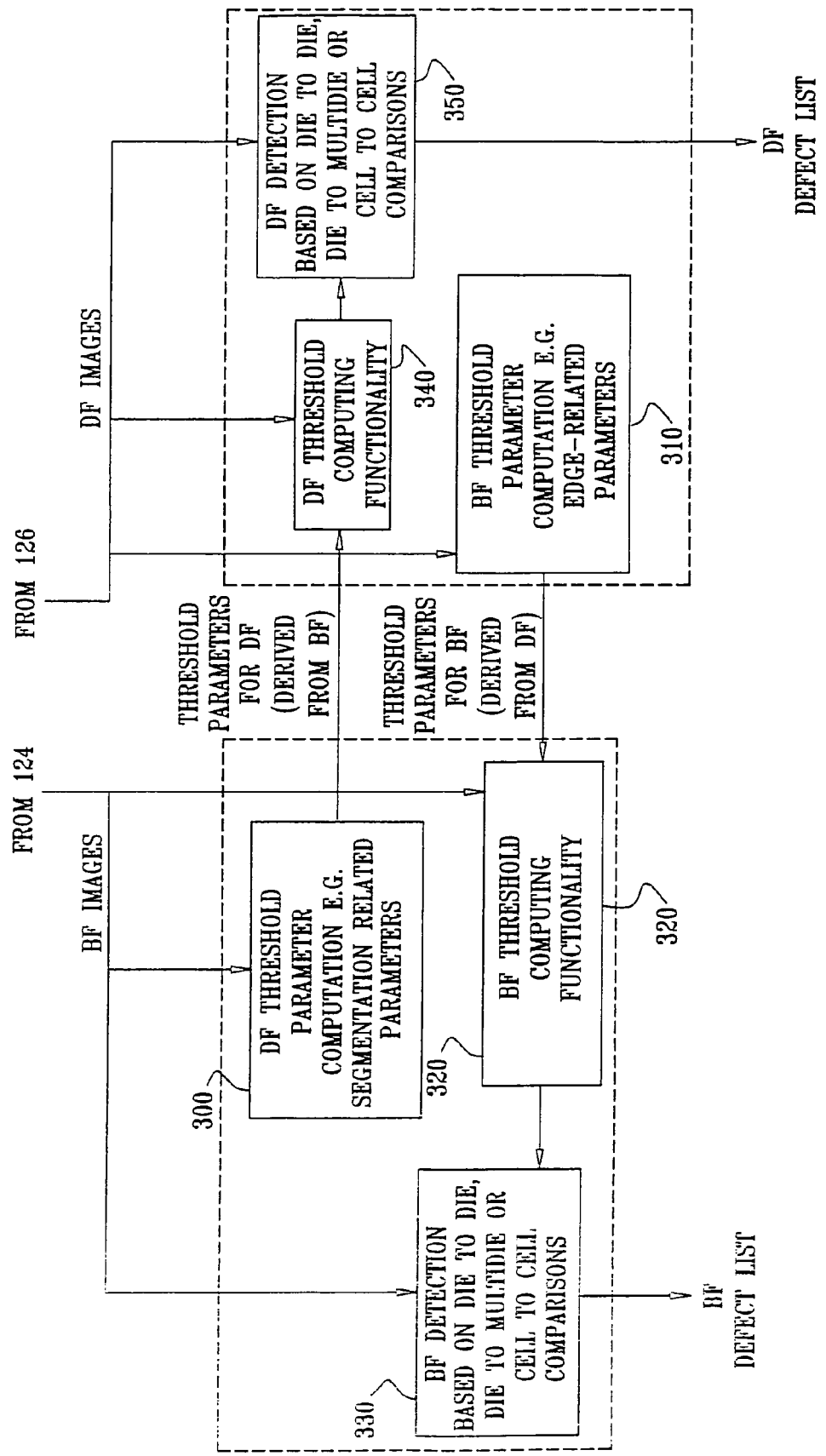
FIG. 9 is a simplified block diagram illustration of the image information combiner of FIGS. 6 and 7, constructed and operative in accordance with a preferred embodiment of the present invention, in which threshold data is passed from one channel to another.

Reference is now made to FIG. 9 which is a simplified block diagram of a preferred implementation of the image information combiner 128 of FIGS. 6 and 7. The image information combiner 128 accepts BF images from image memory 124 (or more generally, images in a first illumination mode) and DF images (or, more generally, images in a second illumination mode) from image memory 126. A DF threshold parameter computation unit 300 accepts BF information and computes therefrom parameters e.g. segmentation-related parameters, which are pertinent to determination of the threshold of defect detection for the DF inspection process.

A BF threshold parameter computation unit 310 accepts DF information and computes therefrom, parameters, e.g. edge-related parameters, which are pertinent to determination of the threshold of defect detection for the BF inspection process. A BF threshold computer 320 accepts threshold parameters from BF threshold parameter computation unit 110 and BF images and uses this information to compute a threshold to govern BF defect detection performed by unit 330, thereby to yield a BF defect list. A DF threshold computer 340 accepts threshold parameters from DF threshold parameter computation unit 300 and DF images and uses this information to compute a threshold to govern DF defect detection performed by unit 350, thereby to yield a DF defect list. The defect detection processes performed by units 330 and 350 may for example be based on die to die comparison methods, die to multi-die comparison methods or cell to cell comparison methods. Suitable defect detection methods are known in the art and also are described in coassigned U.S. patent application Ser. No. 11/069,712, entitled "Method and apparatus for detecting defects in wafers" and in coassigned U.S. patent application Ser. No. 11/068,711 entitled "Method and apparatus for detecting defects in wafers including alignment of the wafer images so as to induce the same smear in all images", both filed 28 Feb. 2005, both incorporated herein by reference.

The apparatus of FIG. 9 is suitable for implementing use of a DF image, where the edges of the features tend to be enhanced in order to define the borders between the substrate and the features to restrict the BF detection only to a specific portion of the wafer. For instance when inspecting metal layers, there is a dielectric thickness variation in different zones on the wafer. In many cases these thickness variation do not have any real effect on the device performance and are not considered defects but rather nuisance. The thickness variation of the dielectric cause a large variation of the reflected signal from the dielectric due to thin film effect. This makes any die to die comparison very inefficient. Using the features' edge information obtained from the DF image the detection sensitivity on the dielectric zones can be reduced such that the inspection will be less sensitive to the nuisance effect of thickness variation.

Another example of advantageous use of information flowing in from one mode of inspection to affect selection of defect detection threshold for another mode of inspection, as shown in FIG. 9, is for handling of metal grains. Metal grains tend to occur on metal lines and are considered nuisance such that it is preferable that such metal grains should not trigger the system's defect alarm. However, in dark field illumination mode, metal lines are substantially indistinguishable from dielectric and therefore, metal grains tend to trigger defects similarly to genuine defects occurring on dielectric portions. In contrast, in bright field mode, metal lines are easily distinguishable from dielectric portions of the object such that the object can easily be segmented or partitioned into separate areas namely metal line zones and dielectric zones. According to a preferred embodiment of the present invention, the threshold computation unit of the dark field inspection computes a higher threshold for metal line zones in which reduced sensitivity is desirable, relative to dielectric zones in which increased sensitivity is desirable.

Figure 10A:
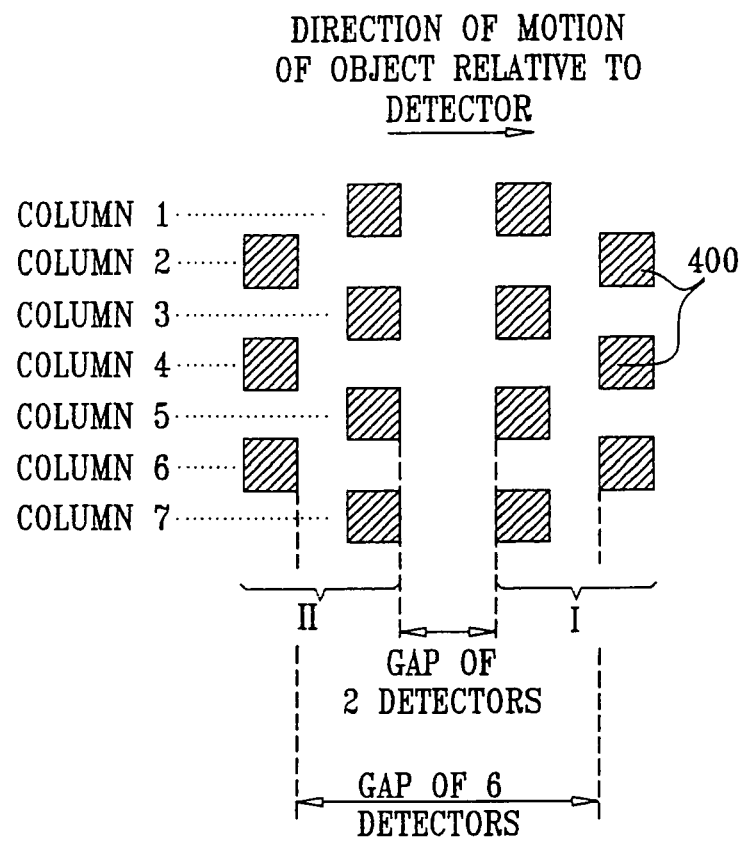
FIGS. 10A and 10B are pictorial illustrations of a two-dimensional arrangement of the detector arrays of FIG. 6 or 7, constructed and operative in accordance with a preferred embodiment of the present invention.

FIG. 10A is an array of detector active areas 400, constructed and operative in accordance with a preferred embodiment of the present invention. The detector assemblies 105 of FIG. 6 or 145 of FIG. 7 may be constructed to yield the active areas shown in FIG. 10A. As shown, the active areas in FIG. 10 are arranged in a plurality of columns, specifically 7 columns, each arranged in the direction of motion of the object relative to the detector, thereby to allow a slice of the object which is 7 times as wide as the active area, to be scanned simultaneously. To simplify the detector optics, the active areas are not adjacent. In the illustrated embodiment, there is a gap of two active areas, or an integer multiple thereof, in every second column (e.g. columns 1, 3, 5 and 7), and a gap of six active areas, or an integer multiple thereof in every other second column (e.g. columns 2, 4 and 6).

Figure 10B:
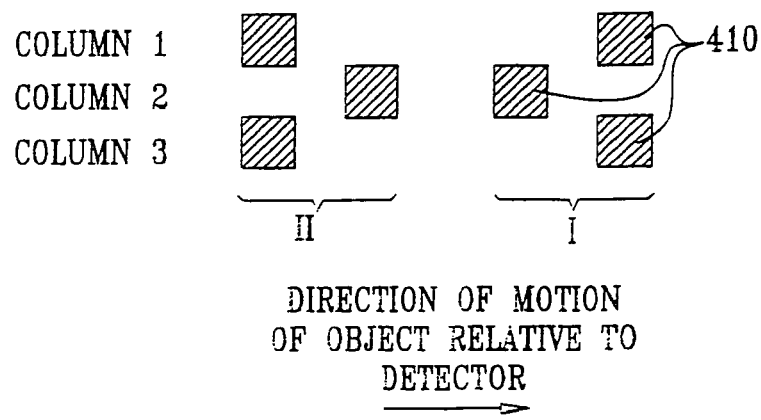

FIG. 10B is an array of detector active areas 410, constructed and operative in accordance with a preferred embodiment of the present invention. The detector assemblies 105 of FIG. 6 or 145 of FIG. 7 may be constructed to yield the active areas shown in FIG. 10B. As shown, the active areas in FIG. 10A are arranged in 3 columns, each arranged in the direction of motion of the object relative to the detector thereby to allow a slice of the object which is 3 times as wide as the active area, to be scanned simultaneously. To simplify the detector optics, the active areas are not adjacent. In the illustrated embodiment, there is a gap of two active areas, or an integer multiple thereof, in every second column (e.g. column 2), and a gap of six active areas, or an integer multiple thereof in every other second column (e.g. columns 1 and 3).

Generally, an array of detector active areas designed to simultaneously scan an object slice n active areas wide, may comprise a first group, I, of non-adjacent active areas entirely covering the slice a first time, and a second group II, of non-adjacent active areas, entirely covering the slice a second time, and spaced an even number of active areas behind the first group, along the direction of motion of the object relative to the detector. The even number of active areas separating the first group from the second group ensures that an intermittent pulse schedule, including a sequence of first illumination mode pulses at times t0, t2, t4, . . . interspersed with a sequence of second mode pulses at times t1, t3, t5, . . . will result in the entire slice beings covered in both illumination modes.

Figure 12A:
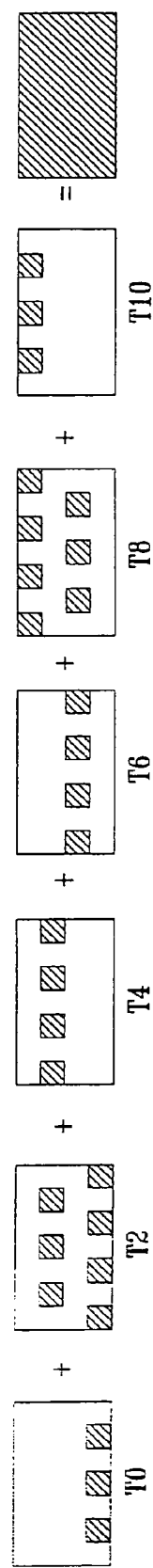
FIG. 12A is a pictorial illustration showing the full coverage in the first illumination mode, provided by the scanning sequence of FIG. 11.
Figure 12B:
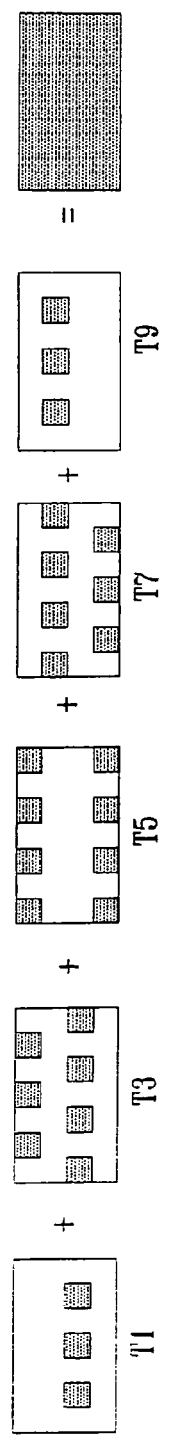
FIG. 12B is a pictorial illustration showing the full coverage, in the second illumination mode, provided by the scanning sequence of FIG. 11.
Figure 13A:
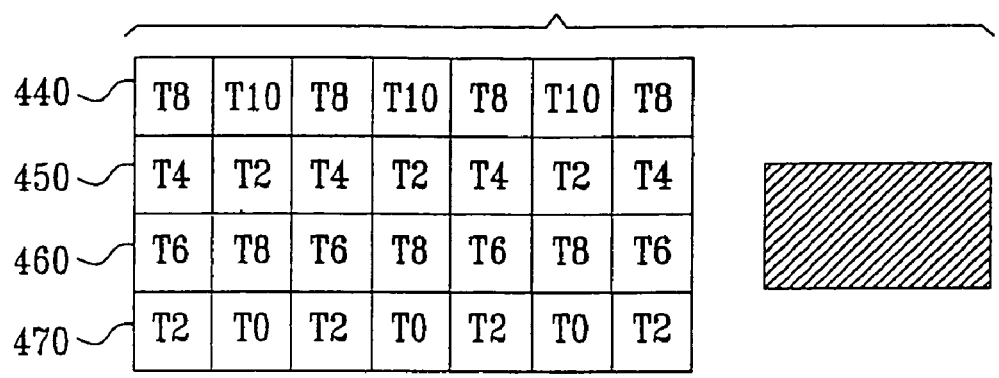
FIG. 13A is a diagram showing the pulse times at which each location within an object portion is covered by the first illumination mode, from among the following pulse times: t0, t2, t4, t6, t8, t10, at which the first illumination mode is active.
Figure 13B:
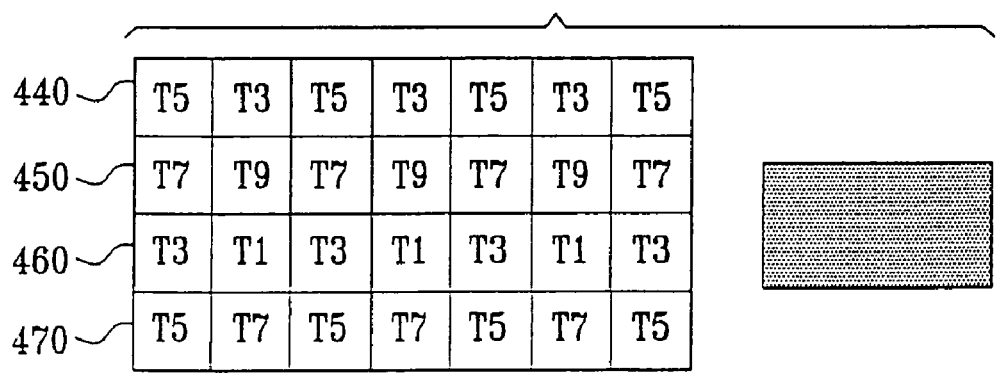
FIG. 13B is a diagram showing the pulse times at which each location within an object portion is covered by the second illumination mode, from among the following pulse times: t1, t3, t5, t7 and t9, at which the second illumination mode is active.

FIG. 11 is a pictorial illustration of a scanning sequence employing two modes of illumination and the two-dimensional detector array which entirely covers the inspected feature in the field of view of FIG. 10A. FIG. 12A is a pictorial illustration shown, the full coverage, in the first illumination mode, provided by the scanning sequence of FIG. 11. FIG. 12B is a pictorial illustration showing the full coverage, in the second illumination model, provided by the scanning sequence of FIG. 11. FIG. 13A is a diagram showing the pulse times at which each location within an object portion is covered by the first illumination mode, from among the following pulse times: t0, t2, t4, t6, t8, t10, at which the first illumination mode is active. FIG. 13B is a diagram showing the pulse times at which each location within an object portion is covered by the second illumination mode, from among the following pulse times: t1, t3, t5, t7 and t9, at which the second illumination mode is active.

FIGS. 11, 12A and 12B show how a slice which is 7 active areas wide is covered completely by using the detector array of FIG. 10A. In FIG. 11 the rectangles 420 represent a portion of the field of view illuminated by the first illumination mode. The same portion of the field is denoted 430 when it is illuminated by the second illumination mode. The widths of rectangles 420 and 430 are chosen to fill the width of the scanning slice. The first mode of illumination is indicated by diagonal lines and the second mode of illumination is indicated by dots, respectively. As shown, the first mode of illumination, denoted by diagonal lines, operates in pulses occurring at times t0, t2, t4, t6, . . . and the second mode of illumination, denoted by dots, operates in pulses occurring at times t1, t3, t5, . . . .

FIG. 13A is a diagram of pulse times at which each location within an object portion is covered by the first illumination mode. FIG. 13A illustrates that in the embodiment of FIGS. 11-12B, each 4 active area long, 7 active area wide rectangular portion of the object, is completely covered by the first mode of illumination. Since this is the case for each such portion, and since the entire object may be covered by imaginary rectangular portions as above, it follows that the object is completely covered by the first mode of illumination such that preferably, each portion of the object is imaged as seen under the first mode of illumination. As shown, in this example, the first row 440 is imaged in the first mode of illumination at pulses t8 and t10. The second row 450 is imaged in the first mode of illumination at pulses t2 and t4. The third row 460 is imaged in the first mode of illumination at pulses t6 and t8. The fourth row 470 is imaged in the first mode of illumination at pulses t0 and t2. FIG. 13B illustrates complete coverage of 4 rows of a 7 active area wide slice of the object, by the second mode of illumination. As shown, the first row 440 is imaged in the second mode of illumination at pulses t0 and t5. The second row 450 is imaged in the second mode of illumination at pulses t7 and t9. The third row 460 is imaged in the second mode of illumination at pulses t1 and t3. The fourth row 470 is imaged in the second mode of illumination at pulses t5 and t7.

In FIGS. 11-13B, the relative motion between the object and the detector, between pulses, equals the detector dimension in the axis of motion. In FIG. 11, for the two illumination modes, the motion step is of a single detector size. In the embodiment of FIGS. 14A-14B described below, in contrast, the motion step is double the size of the detector.

FIG. 14A is a pictorial illustration of a scanning sequence employing only one mode of illumination and the two-dimensional detector array which entirely covers the inspected feature of view of FIG. 10A. FIG. 14B is a pictorial illustration showing the full coverage provided by the scanning sequence of FIG. 11. FIG. 14C is a diagram showing the pulse times at which each location within an object portion is covered by the single illumination mode, from among the following pulse times: t0, t1, t2, t3, t4 and t5.

FIG. 14A illustrates the image of an object in the field of view, illuminated in a single illumination mode, using the detector array of FIG. 10A. Relative motion between the object and the detector, between pulses, is twice the detector dimension along the axis of motion. Pulses occur at equally spaced times t0, t1, t2, t3, . . . . The portions of the object acquired at each pulse are shown in FIG. 14B. As shown, full, rapid coverage is achieved. FIG. 14C shows the complete coverage of an arbitrary 4-row×7-column portion of the object, wherein the smaller dimensions of each row and column are the same as the dimensions of one active area. As shown, the first row 440 is imaged at pulses t0 and t1. The second row 450 is imaged at pulses t3 and t4. The third row 460 is imaged at pulses t1 and t2. The fourth row 470 is imaged at pulses t4 and t5. Since each such arbitrary portion of the image is covered similarly, it follows that the entire image is covered.

A particular advantage of a preferred embodiment of the present invention is that the detector assembly may comprise detectors which do not "look at" adjacent areas, preferably including even diagonally adjacent areas, thereby obviating much of the mechanical and optical apparatus of co-assigned U.S. Pat. No. 6,694,664 to Neumann, but nonetheless still providing high throughput.

Preferred embodiments of the present invention are particularly suited for applications in which it is desirable for different portions of an object to be inspected in different illumination modes. For example, in DRAM wafer inspection, the DRAM array portion of the die may best be inspected in dark mode, whereas the peripheral area of the die may best be inspected in bright mode.

It is appreciated that the software components of the present invention may, if desired, be implemented in ROM (read-only memory) form. The software components may, generally, be implemented in hardware, if desired, using conventional techniques.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the alt upon reading the specification and which are not in the prior art.

The invention claimed is:

1. An inspection system for inspecting an object, the system comprising:
    an illuminator including at least one pulsed light source, said illuminator being operative to selectively provide a plurality of modes of illumination according to an illumination schedule;
    a detector assembly comprising a plurality (n) of 2-dimensional detectors; and a relative motion provider operative to provide motion of the object relative to the detector assembly, along an axis of motion according to a motion schedule, wherein said motion schedule and said illumination schedule are selected to provide images of at least part of said object in at least two of said plurality of modes of illumination; wherein one of said plurality of 2-dimensional detectors images a first location on said object and another one of said plurality of 2-dimensional detectors images a second location on said object, such that said first location and said second location adjoin.

2. A system according to claim 1 wherein the illumination schedule comprises a sequence of pulses, wherein exactly one of the modes of illumination operates per pulse, in a predetermined order.

3. A system according to claim a 1 wherein said detector assembly comprises a single detector and wherein said plurality of 2-dimensional detectors comprise equal-sized portions of said single detector defined in a linear sequence along the axis of motion.

4. A system according to claim 1 wherein said illuminator comprises a single light source directed, according to said illumination schedule, toward a plurality of illumination optics corresponding to the plurality of modes of illumination respectively.

5. A system according to claim 1 wherein the detector assembly generates an output representing the object, the system also comprising a defect detector operative to detect defects in the output of the detector assembly.

6. A system according to claim 1, wherein said motion schedule and said illumination schedule are selected to provide images of the entirety of said object in each of said plurality of modes of illumination.

7. A system according to claim 1 wherein said at least one pulsed light source comprises a plurality of light sources.

8. A system according to claim 7, wherein each of said plurality of light sources is operative to provide a different one of said plurality of modes of illumination.

9. A system according to claim 1, wherein said plurality of modes of illumination includes at least one dark mode.

10. A system according to claim 1 wherein said plurality of modes of illumination includes at least one bright mode.

11. A system according to claim 1, wherein said plurality of modes of illumination includes a plurality of dark modes, differing in their polarizations.

12. A method for inspecting an object, the method comprising:

operating an illuminator, including at least one pulsed light source, and being operative to selectively provide a plurality of modes of illumination according to an illumination schedule;

operating a detector assembly comprising a plurality of 2-dimensional detectors; and providing motion of the object relative to said detector assembly, along an axis of motion, in accordance with a motion schedule wherein said motion schedule and said illumination schedule arc selected to provide images of at least part of said object in at least two of said plurality of modes of illumination thereby inspecting said object;

wherein said plurality of modes of illumination includes first and second modes of illumination and wherein at least one first threshold of value is used to filter candidate defects thereby, to generate a first defect list from images generated in the first mode of illumination, and at least one second threshold value is used to filter candidate defects, thereby to generate a second defect list from images generated in the second mode of illumination and wherein said at least one first threshold value used in at least a first image portion is determined at least partly by information characterizing said at least one first image portion as illuminated in said second mode of illumination and wherein said at least one second threshold value used in at least a second image portion is determined at least partly by information characterizing said at least one second image portion as illuminated in said first mode of illumination.

* * * * *